United States Patent [19]

Okugawa

[11] Patent Number: 5,452,079
[45] Date of Patent: Sep. 19, 1995

[54] METHOD OF AND APPARATUS FOR DETECTING DEFECT OF TRANSPARENT SHEET AS SHEET GLASS

[75] Inventor: Shinya Okugawa, Matsusaka, Japan

[73] Assignee: Central Glass Company, Limited, Yamaguchi, Japan

[21] Appl. No.: 81,872

[22] Filed: Jun. 25, 1993

[30] Foreign Application Priority Data

Jun. 26, 1992 [JP] Japan .................................. 4-169456
May 14, 1993 [JP] Japan .................................. 5-113251

[51] Int. Cl.[6] .......................................... G01N 21/89
[52] U.S. Cl. ................................. 356/237; 356/429; 356/430; 250/559.42
[58] Field of Search ..................... 356/237, 429, 430; 250/572, 562, 563

[56] References Cited

U.S. PATENT DOCUMENTS

| | | | |
|---|---|---|---|
| 3,799,679 | 3/1974 | Simko | 356/237 |
| 3,814,946 | 6/1974 | Takahashi et al. | 356/430 |
| 4,492,477 | 1/1985 | Leser | 356/239 |
| 4,647,197 | 3/1987 | Kitaya et al. | 356/239 |
| 5,216,481 | 6/1993 | Minato | 250/223 B |
| 5,243,400 | 9/1993 | Ringlien | 356/428 |

FOREIGN PATENT DOCUMENTS

| | | | |
|---|---|---|---|
| 0416302 | 3/1991 | European Pat. Off. | 356/429 |
| 0484237 | 5/1992 | European Pat. Off. | 356/237 |
| 61-176838 | 8/1986 | Japan | 356/429 |
| 61-176839 | 8/1986 | Japan | 356/429 |
| 1-189549 | 7/1989 | Japan | 356/237 |
| 1-216241 | 8/1989 | Japan | 356/237 |
| 2-36339 | 2/1990 | Japan | 356/237 |
| 3-27343 | 3/1991 | Japan | 356/237 |

*Primary Examiner*—William Mintel
*Assistant Examiner*—Minhloan Tran
*Attorney, Agent, or Firm*—Keck, Mahin & Cate

[57] ABSTRACT

A light source casts light on a transparent sheet through a slit plate. A camera which is focused at a distance nearer than the transparent sheet or remoter than the slit plate, receives the light transmitted through the transparent sheet and picks up an image of a defect of the transparent sheet. An image processing unit inspects the image for a defect of the transparent sheet as "knots", "cords", etc.

16 Claims, 6 Drawing Sheets

METHOD OF AND APPARATUS FOR DETECTING DEFECT OF TRANSPARENT SHEET AS SHEET GLASS

BACKGROUND OF THE INVENTION

1. Field of the Invention

The present invention relates to a method of and apparatus for detecting, among various defects of a transparent sheet, a defect that is caused by distortion such as "knots", "cords" or "striae", unmelted particles or "stones", "bubbles", etc.

2. Description of the Prior Art

A known method utilizes a one-dimensional camera for detecting a shadow caused by interception of light by an internal or surface defect of a transparent sheet as disclosed in Japanese Patent Provisional Publication No. 1-189549. Another known method utilizes a point light source for casting a light through a transparent sheet on a screen and a sensor for detecting a defect in a projected figure as disclosed in Japanese Utility Model Provisional Publication No. 3-27343. A further known method is adapted to observe a row of parallel lines through a transparent sheet so that due to a difference in refraction a defect is represented by distortion of the lines as disclosed in Japanese Patent Provisional Publication Nos. 61-176838 and 61-176839. A further known method utilizes transmission and reflection of a laser beam for detection of a defect of a transparent sheet.

A problem of the prior art methods is that a fleck of dirt, etc. on a transparent sheet is erroneously judged as a defect caused by "knots", "cords", "stones", "bubbles", etc.

SUMMARY OF THE INVENTION

According to an aspect of the present invention, there is provided a method of detecting a defect of a transparent sheet wherein a light source casts light on the transparent sheet through a screen having a row of alternate light transmitting portions and shading portions and a camera receives the light transmitted through the transparent sheet and produces an image for inspection of the defect, characterized in that the camera is focused at a distance less than that to the transparent sheet or more than that to the screen.

According to another aspect of the present invention, there is provided an apparatus for detecting a defect of a transparent sheet, which comprises surface light source means located on one of opposite sides of the transparent sheet, slit means located adjacent to the surface light source means so that light from the surface light source is cast therethrough on the transparent sheet, and camera means located on the other of the opposite sides of the transparent sheet for forming an image of the defect by directly receiving the light transmitted through the slit means, in which the camera means is focused at a distance nearer than the transparent sheet or remoter than the slit means.

These method and device are effective for solving the above noted problems inherent in the prior art.

It is accordingly an object of the present invention to provide an improved method of detecting a defect of a transparent sheet which does not erroneously judge a fleck of dirt, etc. on a transparent sheet as a defect caused by "knots", "cords", "stones", bubbles", etc.

It is a further object of the present invention to provide a method of detecting a defect of a transparent sheet of the above described character which can effect a reliable operation without requiring a complicated, expensive device and therefore practically quite useful.

It is a further object of the present invention to provide an apparatus for carrying out the method of the above described character.

DETAILED DESCRIPTION OF PREFERRED EMBODIMENTS

Figure 1:
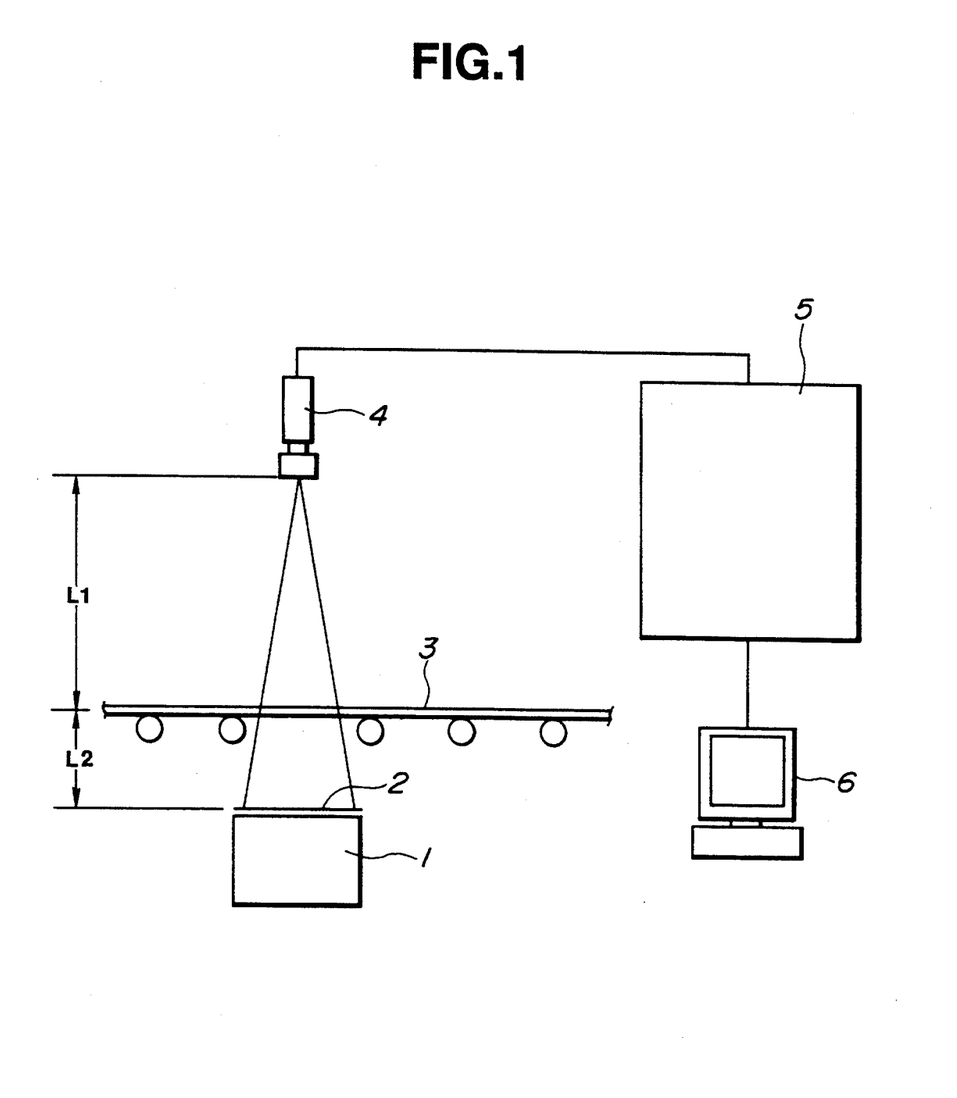
FIG. 1 is a schematic view of an apparatus for carrying out a method of detecting a defect of a transparent sheet according to an embodiment of the present invention.
Figure 2:
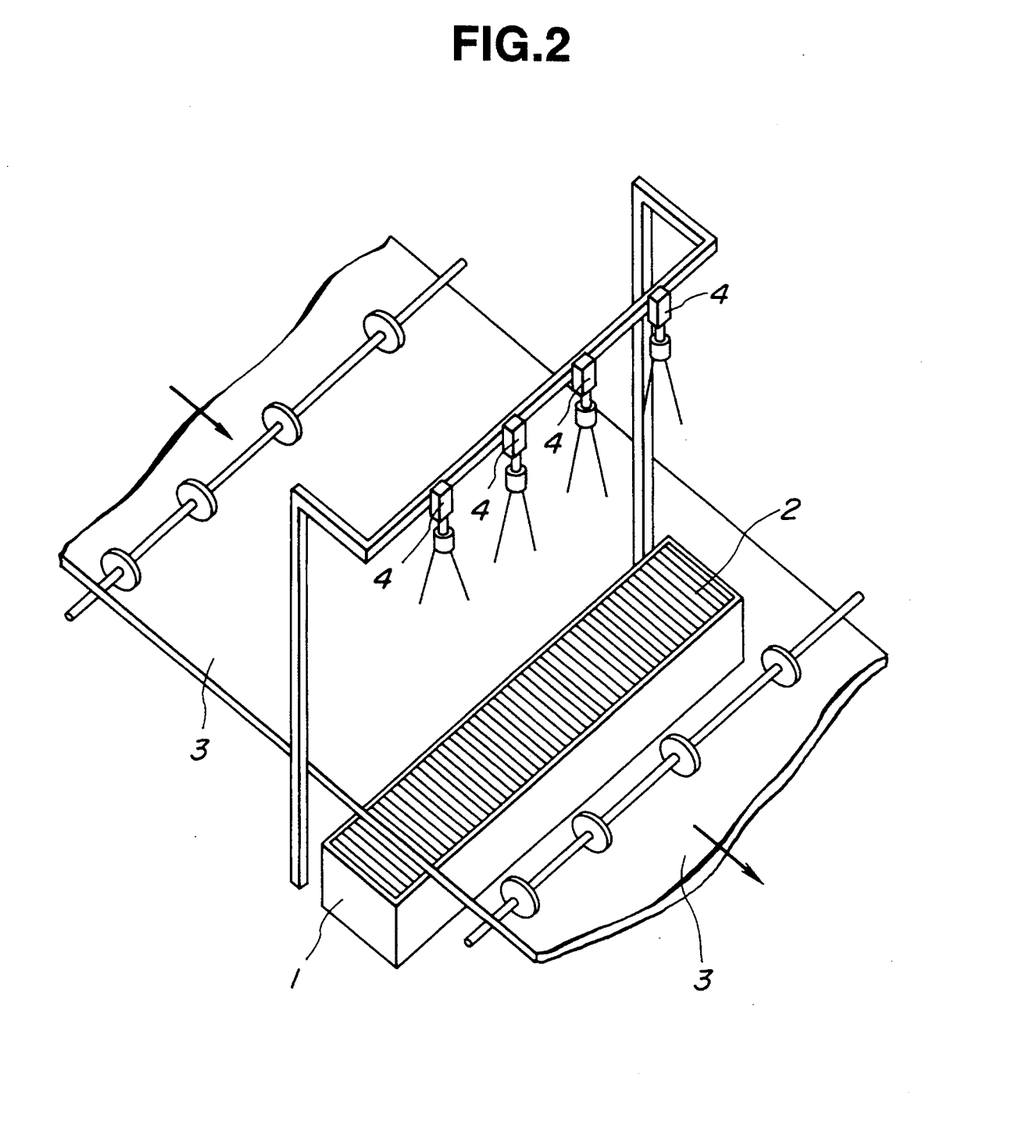
FIG. 2 is a perspective view of a principal portion of the apparatus of FIG. 1.

Referring first to FIGS. 1 and 2, a light source 1 consists of a box having an upper opened end face, a plurality of light sources, e.g., a plurality of fluorescent lamps installed in the box and a white diffusion plate attached to the upper end face of the box. A slit plate 2 includes a plurality of alternate light transmitting portions and shading portions in the form of a row of fine parallel lines which are arranged in parallel to or obliquely to the direction of conveyance or running of a transparent sheet or plate 3 as a sheet glass for inspection. The light transmitting portions are constituted by slit-like parallel openings of the width of 0.25 mm. The shading portions are provided between the light transmitting portions and have the width of 0.5 mm. The slit plate 2 is formed from a transparent sheet or plate and formed with the light transmitting portions and shading portions by printing or otherwise applying to the surface thereof ink, paint, paste, etc. The slit plate 2, in use, is laid on the above described white diffusion plate and bonded or otherwise secured thereto and is sized so as to be larger in width than the transparent sheet 3 for inspection. As seen from FIG. 2, the light source 1 with the slit plate 2 is arranged so as to extend across the transparent sheet 3 at right angles. Another light source may be used so long as it is a surface light source in place of the above described light source 1.

A plurality of two-dimensional cameras 4 using CCD (charge coupled device) are arranged in line so as to oppose to the light source 1, i.e., in line extending across the transparent sheet 3 while interposing therebetween the transparent sheet 3. Each camera 4 is set perpendicularly to the upper face of the transparent sheet 3 and in such a manner that its scanning lines are parallel to the direction in which the transparent sheet 3 is conveyed or runs so that the light having transmitted through the light transmitting portions of the slit plate 2 can be taken as a two-dimensional field of view. The plurality of cameras 4 are arranged as above in order to obtain a field of view covering the width of the transparent sheet 3. The two-dimensional cameras 2 output signals to an image processing unit 5 which inspects an image produced by the cameras 4 for the defect of the transparent sheet 3.

Figure 3:
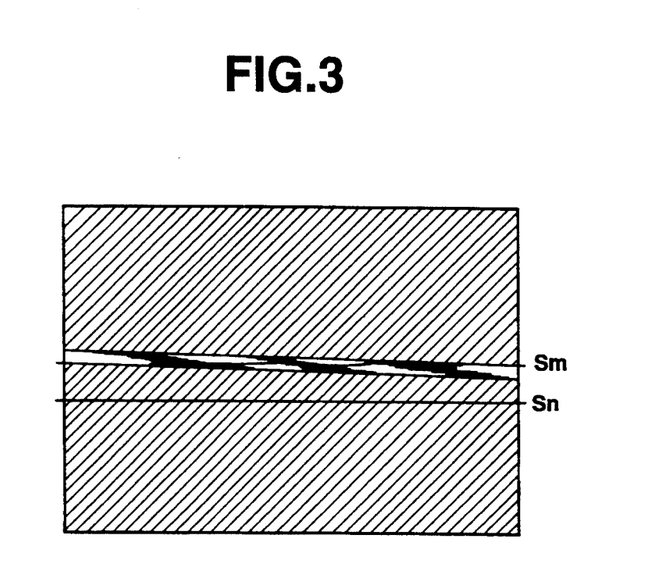
FIG. 3 is an image produced by a two-dimensional camera when a defect is "cord"

When the transparent sheet 3 has at a certain place a defect of "cord" for instance, corresponding one of the cameras 4 produces such an image shown in FIG. 3.

Figure 4:
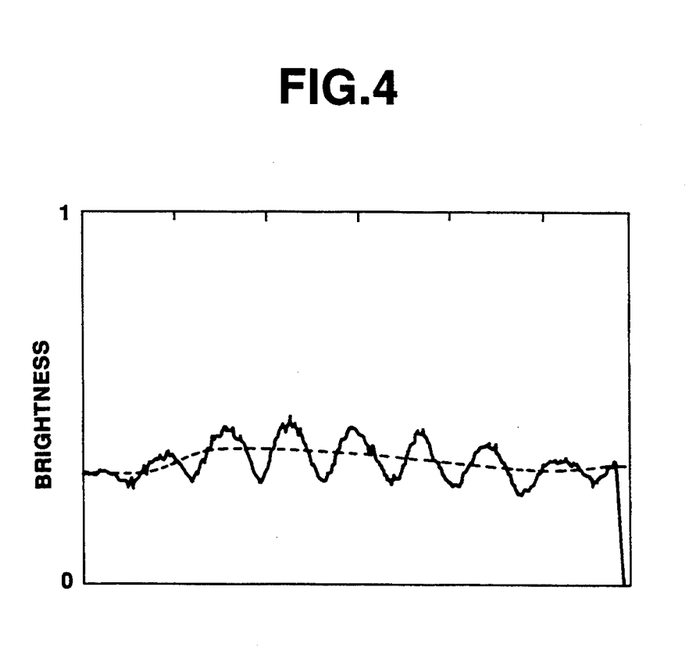
FIG. 4 is a graph of a variation of light and dark level produced by an image processing device in response to the signals produced by a two-dimensional camera when a defect is "cord"

In FIG. 4, a solid line represents variations of the brightness or luminance of the scanning line Sm whilst the dotted line represents variations of the luminance of the scanning line Sn, in which the data are plotted with the luminance as ordinate and in which the luminance becomes zero (0) when the camera 2 is kept out of light and the maximum luminance is "1". From the graph of FIG. 4, it is found that a defect of "stria" is located on the scanning line Sm whilst there is no defect on the scanning line Sn. The luminance of the scanning line Sn is intermediate between light and dark as indicated by the dotted line, whereas the luminance of the scanning line Sm varies alternately to include light portions (peak) and dark portions (bottom) which appear alternately. From the variations of the luminance of the scanning line Sm, it is found that there are continuous defects along this scanning line. Though only two scanning lines Sm and Snare shown in FIGS. 3 and 4 for the convenience of explanation, there are actually provided a number of scanning lines. Further, the striped pattern otherwise caused by the alternate light transmitting portions and shading portions of the slit plate 2 do not appear since each camera 4 is not focused at a distance to the slit plate 2, i.e., each cameras 4 is not focused on the slit plate 2.

In this connection, it is to be noted that the present invention is based on such a discovery that when each camera 4 is focused at a distance other than the distances to the slit plate 2 and the transparent sheet 3 and where interference fringes due to the slit plate 2 are not caused it produces such an image in which a transparent sheet portion having a defect has a larger or smaller brightness than that of a transparent sheet portion having no defect, so that by focusing the camera at such a distance it becomes possible to assuredly detect a defect of the transparent sheet 3 as "cords" or "striae". This is because when the camera 4 is focused at a distance (e.g., a focal distance within the range of "A" and "B" in FIG. 5) other than the distances to the slit plate 2 and the transparent sheet 3 the background of the image produced by the camera 4, which corresponds to a transparent sheet portion having no defect, has such a brightness intermediate between light and dark and colored in gray, whereas a portion of the image corresponding to a transparent sheet portion having a defect as distortion or chemical inhomogenity has such a brightness larger or smaller than the background luminance due to diffraction, interference, etc. of transmitted light through the transparent sheet 3. When the camera 4 is focused at a distance nearer than the transparent sheet 3, the difference in brightness between the background and a portion indicative of a defect becomes larger, thus making it possible to recognize the defect with ease.

Further, it is to be noted that since each camera 4 is not focused on the transparent sheet 3 erroneous detection of a fleck of dirt, etc. is assuredly prevented according to the present invention.

The image produced in each camera 4 is divided, along 512 scanning lines and along 512 sections of each scanning line, into 512×512 blocks, so the brightness of each blocks from the leftmost and uppermost one to the rightmost and lowermost one is represented numerically and stored in a memory, and by using a brightness filter of the image processing unit 5 the difference between the maximum brightness in a group of blocks (e.g., 3×3 blocks) and the background brightness and the difference between the minimum brightness of the group of blocks and the background brightness are computed.

The difference is expressed in a binary form, i.e., by "1" when larger than a predetermined value and by "0" when smaller. After the binary processing, it is judged whether the blocks for which the signal "1" indicative of a defect is produced are continuous vertically, horizontally or obliquely, and when the blocks are judged continuous the length and area of the defect are computed from the coordinates of the blocks. When the defect is continuous in the direction of scanning, it is judged as "cord", and when not continuous it is judged as a point defect.

Further, the data relating to the kind, size, etc. of the above described defect are output to a personal computer 6, etc. for performing integrated control of various informations. Further, the defect can be detected instantly and its location can be specified, so a portion having a defect is marked for detection and automatic cutoff in the following process.

Figure 5:
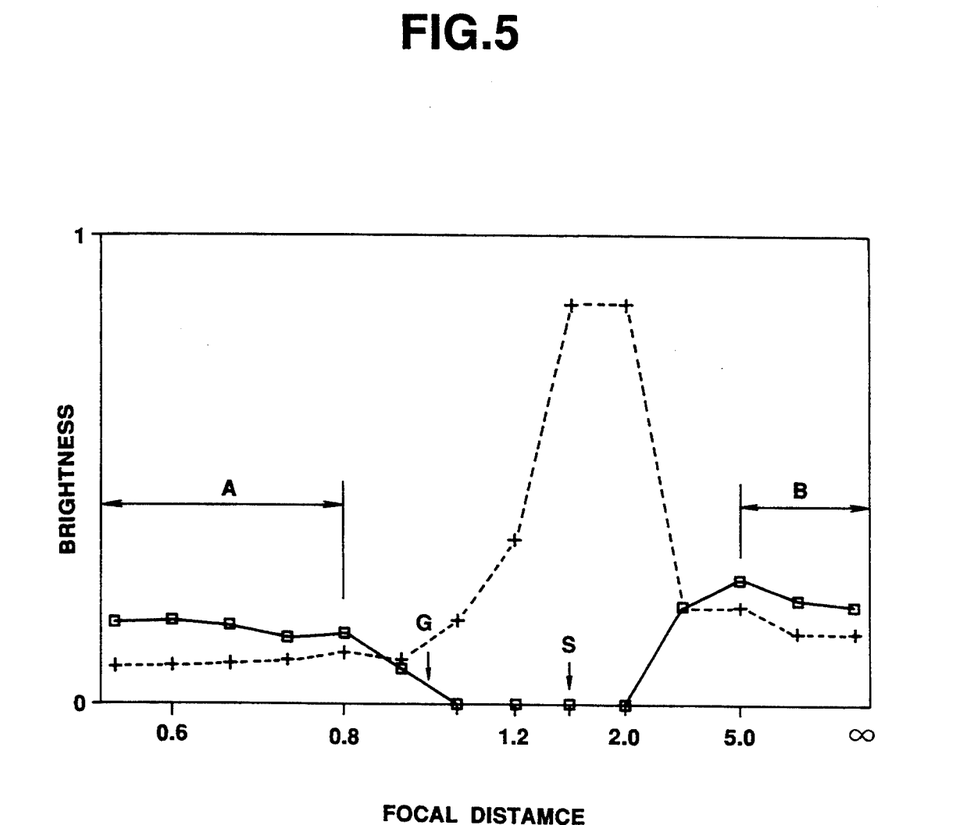
FIG. 5 is a graph of an intensity of a defect and a noise level of a portion having no defect in relation to a focal point of a camera.

An exemplified usage of such a device will be described. It is set such that the distance L1 between each camera 4 and the transparent sheet 3 is 1000 mm, the distance L2 between the transparent sheet 3 and the slit plate 2 is 600 mm, the width of each shading portion of the slit plate 2 is 0.5 mm, the width of each light transmitting portion of the slit plate 2 is 0.25 mm, the diaphragm opening F of the camera 4 is 5, and the focal distance f is 25 mm. By changing the focus of the camera 2 variously, an exemplified defect which is a slight "cord" is treated by the above described image processing and expressed by a binary form in which "0" represents the case where the camera 4 is kept out of light and "1" represents the maximum brightness, whereby such a result represented by a solid line in FIG. 5 is obtained. Under the same condition, the brightness of the portion having no defect is measured, whereby such a result represented by the dotted line in FIG. 5 is obtained.

The focal distance of "1" (the position indicated by "G" in FIG. 5) indicates that each camera 4 is focused at a distance to the transparent sheet 3, i.e., each camera 4 is focused on the transparent sheet 3. On the other hand, the focal distance of "S" indicates that each camera 4 is focused at a distance to the slit plate 2, i.e., each camera 4 is focused on the slit plate 2. When each camera 4 is focused at a distance to the slit plate 2 or the distance adjacent thereto, the background brightness (i.e., the brightness corresponding to the sheet glass portion having no defect) is sharply increased as seen from the intermediate portions of the dotted line curves in FIG. 5. This is because the alternate light portions (white) and dark portions (black) due to the slit plate 2 constitute an interference fringe in the form of stripes and therefore a noise or disturbance in detection of a defect of a transparent sheet. Thus, when each camera 4 is focused at a distance to the slit plate 2 or the distance adjacent thereto, it is hardly difficult to carry out the detection of a defect. On the other hand, the opposite end portions of the dotted line curve in FIG. 5 are relatively planar, so when the focal distance of each camera 4 is within the ranges "A" and "B", the background brightness is intermediate between light and dark, i.e., the background is colored in gray. Thus, it will be understood that a defect of "cord" or "stria" can be recognized when the focal distance of each camera 4 is in the range "A", i.e., 0.8 or less and in the range "B", i.e., 5.0 or more in which the brightness representative of the transparent sheet portion having a defect becomes larger than the brightness representative of the transparent sheet portion having no defect (i.e., background brightness).

Figure 6:
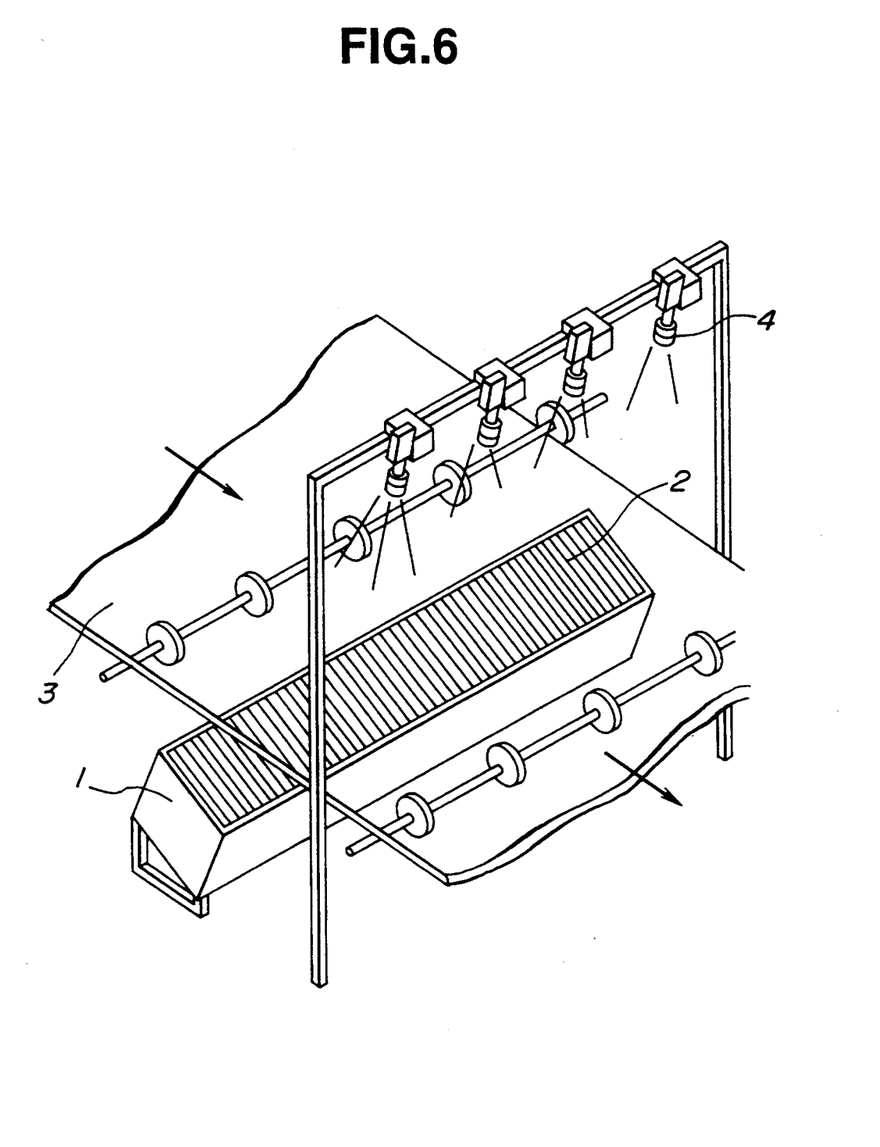
FIG. 6 is a perspective view of an apparatus for carrying out a method according to another embodiment.

FIG. 6 shows another embodiment which is substantially similar to the previous embodiment of FIGS. 1 to 5 except that each camera 4 is not set perpendicularly to the side surface of the transparent sheet but obliquely. This embodiment can produce substantially the same effect to the previous embodiment.

Figure 7:
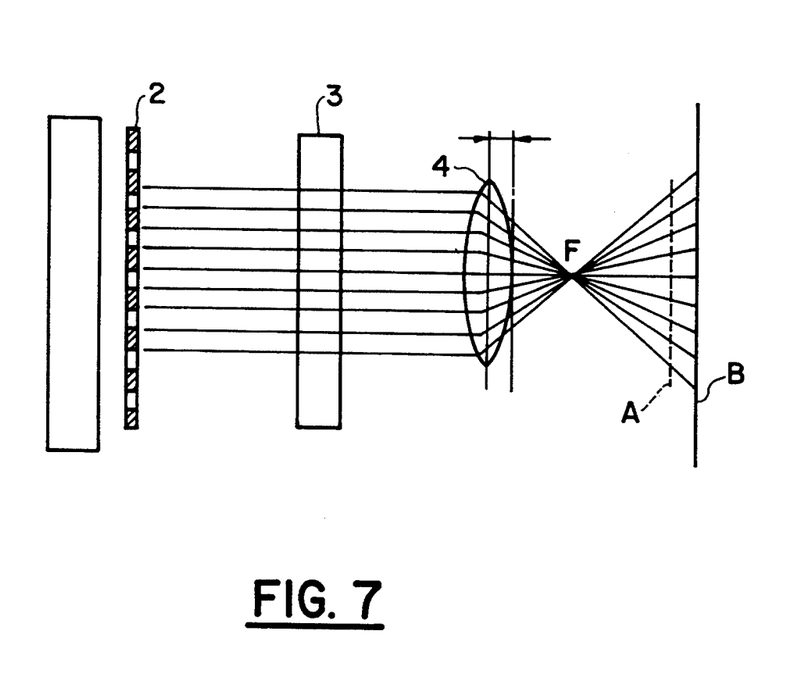
FIG. 7 is a schematic view of an optical system according to the invention.

FIG. 7 illustrates an optical system of the invention. Transparent sheet 3 is disposed between slit plate 2 and camera 4. The focal point of the lens of camera 4 is shown as F. The image of the slit plate 2 would be in focus on plane A. The surface for picking up defects in the transparent plate is image pickup surface B. The image of slit plate 2 is not in focus at image pickup surface B.

In the foregoing, it is to be noted that in contrast to the method disclosed by Japanese Patent Provisional Publication No. 61-176838 a camera is used for directly picking up an image of parallel lines through a transparent sheet (i.e., the camera is focused on the parallel lines) the camera in the method of this invention is not adapted to pick up the image of the slit plate but to pick up the image of a defect of a transparent sheet by the effect of the light passed through the slit plate whereby by the effect of combination of the provision of the slit plate and the above described focusing of the camera the image of the defect is amplified, i.e., becomes more visible or recognizable relative to the background.

While the present invention has been described and shown as above, various modifications and variations may be made thereto without departing from the scope of the appended claims.

For example, the focal point enabling detection of a defect is not limited to the ranges "A" and "B" in FIG. 5, but varies depending upon the optical characteristics of the camera, slit plate, etc.

Further, while the alternate light transmitting portions and shading portions of the slit plate have been described and shown as being in the form of a row of parallel lines, they may otherwise be in the form of a grid or grille or in the form of a meshed screen having a honeycomb structure or a structure consisting of rows of rhombic openings.

Further, the camera is not limited to the type using a CCD but may otherwise be of the type using MOS or an image pickup tube.

Further, while a defect of a relatively large size or intensity can be detected even when the scanning lines are perpendicular to the direction of running of the transparent sheet. However, since a slight "cord" or "stria" defect generally appears nearly in parallel to the direction of running of the transparent sheet, there is a possibility that such a defect cannot be detected when the scanning lines are not parallel to the direction of running of the transparent sheet. So, it is desirable to arrange the scanning lines in parallel to the direction of running of the transparent sheet.

Further, the camera is not limited to a two-dimensional type but cap otherwise be of a one-dimensional type. In such a case, the length of the light source and the slit plate in the direction of running of the transparent sheet can be smaller.

Further, the present invention may be used for detection of a defect of not only sheet glass but a transparent sheet as a transparent plastic sheet.

What is claimed is:

1. A method of detecting a defect of a transparent sheet wherein a light source casts light on the transparent sheet through a screen having a row of alternate light transmitting portions and shading portions and a camera receives the light transmitted through the transparent sheet and produces an image for inspection of the defect wherein an image of said screen is out of focus, characterized in that said camera is set to focus at a distance closer than said transparent sheet or farther than said screen.

2. A method of detecting a defect of a transparent sheet wherein a light source casts light on the transparent sheet through a slit plate having a row of alternate light transmitting portions and shading portions, a camera receives light transmitted through the transparent sheet and produces an image for inspection of the defect wherein an image of said slit plate is out of focus, and an image processing unit inspects the image for the defect of the transparent sheet, characterized in that said camera is focused on a point separated from said slit plate and from said transparent sheet and said camera picks up an image of the defect directly.

3. A method according to claim 2, characterized in that said point on which said camera is focused is closer to said camera than said transparent sheet.

4. A method according to claim 2, characterized in that said point on which said camera is focused is farther from said camera than said slit plate.

5. A method according to claim 2, characterized in that said alternate light transmitting portions and shading portions of said slit plate is in the form of a row of parallel lines arranged in parallel to the direction of conveyance of the transparent sheet.

6. A method according to claim 2, characterized in that a plurality of said cameras are provided and arranged in line extending across the direction of conveyance of the transparent sheet.

7. A method according to claim 6, characterized in that said camera is arranged perpendicularly to said slit plate.

8. A method according to claim 7, characterized in that said slit plate is parallel to said transparent sheet.

9. A method according to claim 7, characterized in that said slit plate is inclined to said transparent sheet.

10. A method according to claim 2, characterized in that said light source is a surface light source.

11. An apparatus for detecting a defect of a transparent sheet, comprising:
   surface light source means located on one of opposite sides of the transparent sheet;
   slit means located adjacent to said surface light source means so that light from said surface light source is cast therethrough on the transparent sheet; and
   camera means located on the other of the opposite sides of the transparent sheet for forming an image of the defect by directly receiving the light transmitted through said slit means, wherein an image of said slit means is out of focus;

in which said camera means is set to focus at a distance separated from the transparent sheet and from said slit means.

12. A device according to claim 11, wherein said slit means comprises a slit plate having a plurality of alternate light transmitting portions and shading portions in the form of a row of parallel lines which are arranged parallel to the direction of conveyance of the transparent sheet.

13. A device according to claim 11, wherein said camera means comprises a plurality of cameras which are arranged in line extending across the direction of conveyance of the transparent sheet.

14. A device according to claim 13, wherein each of said cameras is set perpendicularly to a side surface of said slit plate.

15. A device according to claim 14, wherein said side surface of said slit plate is arranged obliquely to a side surface of the transparent sheet.

16. A device according to claim 11, further comprising image processing means for inspecting said image produced by said camera means for the defect of the transparent sheet.

* * * * *